(12) United States Patent
McCune

(10) Patent No.: US 8,728,018 B2
(45) Date of Patent: May 20, 2014

(54) POST OPERATIVE HINGE BRACE

(75) Inventor: Robert J. McCune, Escalon, CA (US)

(73) Assignee: Top Shelf Manufacturing, LLC, Tracy, CA (US)

( * ) Notice: Subject to any disclaimer, the term of this patent is extended or adjusted under 35 U.S.C. 154(b) by 791 days.

(21) Appl. No.: 12/751,510

(22) Filed: Mar. 31, 2010

(65) Prior Publication Data

US 2010/0256543 A1 Oct. 7, 2010

Related U.S. Application Data

(60) Provisional application No. 61/165,305, filed on Mar. 31, 2009.

(51) Int. Cl.
*A61F 5/00* (2006.01)

(52) U.S. Cl.
USPC .................................. 602/16; 602/23; 602/26

(58) Field of Classification Search
USPC ......................................... 602/16, 20, 23, 26
See application file for complete search history.

(56) References Cited

U.S. PATENT DOCUMENTS

| | | |
|---|---|---|
| 4,856,501 A | 8/1989 | Castillo et al. |
| 4,872,448 A | 10/1989 | Johnson, Jr. |
| 4,886,054 A | 12/1989 | Castillo et al. |
| 4,938,206 A | 7/1990 | Harris et al. |
| 4,938,207 A | 7/1990 | Vargo |
| 4,940,044 A | 7/1990 | Castillo |
| 4,955,369 A | 9/1990 | Bledsoe et al. |
| 4,966,133 A | 10/1990 | Kausek |
| 4,982,732 A | 1/1991 | Morris |
| 4,991,571 A | 2/1991 | Kausek |
| 5,009,223 A | 4/1991 | DeFonce |
| RE33,621 E | 6/1991 | Lamb et al. |
| 5,025,782 A | 6/1991 | Salerno |
| 5,063,916 A | 11/1991 | France et al. |
| 5,074,290 A | 12/1991 | Harris et al. |
| 5,078,127 A | 1/1992 | Daneman et al. |
| 5,085,210 A | 2/1992 | Smith, III |
| 5,086,761 A | 2/1992 | Ingram |
| 5,092,320 A | 3/1992 | Maurer |
| 5,107,823 A | 4/1992 | Fratesi |
| 5,133,341 A | 7/1992 | Singer et al. |
| 5,135,469 A | 8/1992 | Castillo |
| 5,168,865 A | 12/1992 | Radcliffe et al. |
| 5,230,695 A | 7/1993 | Silver et al. |
| 5,267,946 A | 12/1993 | Singer et al. |
| 5,286,250 A | 2/1994 | Meyers et al. |
| 5,292,303 A | 3/1994 | Bastyr et al. |
| 5,302,169 A | 4/1994 | Taylor |
| 5,316,547 A | 5/1994 | Gildersleeve |
| 5,330,418 A | 7/1994 | Townsend et al. |
| 5,356,370 A | 10/1994 | Fleming |
| 5,358,468 A | 10/1994 | Longo et al. |
| RE34,818 E | 1/1995 | Daneman et al. |
| 5,383,843 A | 1/1995 | Watson et al. |
| 5,383,845 A | 1/1995 | Nebolon |
| 5,400,806 A | 3/1995 | Taylor |

(Continued)

*Primary Examiner* — Patricia Bianco
*Assistant Examiner* — Keri J Nelson
(74) *Attorney, Agent, or Firm* — Dickstein Shapiro LLP

(57) ABSTRACT

A hinge brace for supporting and restricting the range of motion of a patient's joint and methods of using the brace. The hinge brace includes a hinge with a first setting arm and second setting arm, corresponding, respectively, to a maximum angle of extension and maximum angle of flexion of the joint. The hinge can be adjusted using a single hand or finger. The hinge can be fitted to a variety of patients by using a telescopic extension mechanism.

22 Claims, 10 Drawing Sheets

(56) References Cited

U.S. PATENT DOCUMENTS

| | | |
|---|---|---|
| 5,433,699 A | 7/1995 | Smith, III |
| 5,458,565 A | 10/1995 | Tillinghast, III et al. |
| 5,462,517 A | 10/1995 | Mann |
| 5,472,413 A | 12/1995 | Detty |
| 5,490,831 A | 2/1996 | Myers et al. |
| 5,514,082 A | 5/1996 | Smith, III |
| 5,514,083 A | 5/1996 | Smith, III |
| 5,520,622 A | 5/1996 | Bastyr et al. |
| 5,527,268 A | 6/1996 | Gildersleeve et al. |
| 5,542,911 A | 8/1996 | Cassford et al. |
| 5,582,584 A | 12/1996 | Billotti |
| 5,586,970 A | 12/1996 | Morris et al. |
| 5,626,557 A | 5/1997 | Mann |
| 5,632,725 A | 5/1997 | Silver et al. |
| 5,641,322 A | 6/1997 | Silver et al. |
| 5,643,185 A | 7/1997 | Watson et al. |
| 5,707,347 A | 1/1998 | Bixler |
| 5,743,865 A | 4/1998 | Townsend |
| 5,766,724 A | 6/1998 | Tailor et al. |
| 5,785,673 A | 7/1998 | Billotti |
| 5,792,084 A | 8/1998 | Wilson et al. |
| 5,800,371 A | 9/1998 | Winn |
| 5,807,294 A | 9/1998 | Cawley et al. |
| 5,857,988 A | 1/1999 | Shirley |
| 5,865,776 A | 2/1999 | Springs |
| 5,865,777 A | 2/1999 | Detty |
| 5,885,235 A | 3/1999 | Opahle et al. |
| 5,943,830 A | 8/1999 | Truitt |
| 5,944,682 A | 8/1999 | Milana-Panopoulos |
| 6,004,283 A | 12/1999 | Young |
| 6,105,531 A | 8/2000 | Knight |
| 6,110,138 A | 8/2000 | Shirley |
| 6,190,341 B1 | 2/2001 | Brim |
| 6,287,269 B1 | 9/2001 | Osti et al. |
| 6,290,664 B1 | 9/2001 | Nauert |
| 6,331,169 B1 | 12/2001 | Bastyr et al. |
| 6,332,224 B1 | 12/2001 | Walker et al. |
| 6,383,156 B1 | 5/2002 | Enzerink et al. |
| 6,387,066 B1 | 5/2002 | Whiteside |
| 6,402,711 B1 | 6/2002 | Nauert |
| 6,413,232 B1 | 7/2002 | Townsend et al. |
| 6,425,166 B1 | 7/2002 | Seligman et al. |
| 6,500,139 B1 | 12/2002 | Townsend et al. |
| 6,527,733 B1 | 3/2003 | Ceriani et al. |
| 6,540,708 B1 | 4/2003 | Manspeizer |
| 6,540,709 B1 | 4/2003 | Smits |
| 6,565,523 B1 | 5/2003 | Gabourie |
| 6,592,538 B1 | 7/2003 | Hotchkiss et al. |
| 6,610,023 B2 | 8/2003 | Steponovich |
| 6,623,439 B2 | 9/2003 | Nelson et al. |
| 6,746,414 B1 | 6/2004 | Devreese |
| 6,796,952 B2 | 9/2004 | Nelson et al. |
| 6,821,261 B2 | 11/2004 | Doty et al. |
| 6,875,187 B2 | 4/2005 | Castillo |
| 6,878,126 B2 | 4/2005 | Nelson et al. |
| 6,890,314 B2 | 5/2005 | Seligman |
| 6,936,019 B2 | 8/2005 | Mason |
| 6,953,442 B2 | 10/2005 | Yamasaki et al. |
| 6,960,175 B1 | 11/2005 | Myers |
| 6,960,177 B2 | 11/2005 | Turrini et al. |
| 6,969,365 B2 | 11/2005 | Scorvo |
| 6,981,957 B2 | 1/2006 | Knecht et al. |
| 6,993,808 B1 | 2/2006 | Bennett et al. |
| 7,004,919 B2 | 2/2006 | Gaylord et al. |
| 7,011,640 B2 | 3/2006 | Patterson et al. |
| 7,022,093 B2 | 4/2006 | Smith et al. |
| 7,037,287 B2 | 5/2006 | Cormier et al. |
| 7,044,925 B2 | 5/2006 | Castillo et al. |
| 7,059,329 B2 | 6/2006 | Mason et al. |
| 7,083,586 B2 | 8/2006 | Simmons et al. |
| 7,097,627 B2 | 8/2006 | Enzerink et al. |
| 7,122,016 B1 | 10/2006 | DeToro et al. |
| 7,128,723 B2 | 10/2006 | Doty et al. |
| 7,192,407 B2 | 3/2007 | Seligman et al. |
| 7,198,610 B2 | 4/2007 | Ingimundarson et al. |
| 7,201,728 B2 | 4/2007 | Sterling |
| 7,235,058 B2 | 6/2007 | Doty et al. |
| 7,235,059 B2 | 6/2007 | Mason et al. |

POST OPERATIVE HINGE BRACE

This application claims the benefit of U.S. Provisional Application Ser. No. 61/165,305, filed Mar. 31, 2009, the entire disclosure of which is incorporated by reference herein.

FIELD OF THE INVENTION

The invention relates to a brace and, more specifically, a post-operative hinged brace.

BACKGROUND OF THE INVENTION

Post operative knee braces are used to control the range of motion of a patient's leg to facilitate recovery after surgery. As shown in FIG. 1, the range of motion 4 for a patient's leg 11 is controlled by a post operative knee brace 1 by providing a maximum extension angle 7 and maximum flexion angle 3 of the patient's leg 11 using a hinge 5. The knee brace 1 can be attached to a patient's leg with straps. The prior art knee brace 1 has an extension setting area 6 and a flexion setting area 12 on opposite sides of a hinge 5. Using an extension setting selector 8, a user can adjust the maximum extension angle 7 of the leg 11 by setting a first selector 8 to a desired angle of extension along the first setting area 13. The user then adjusts the maximum flexion angle 3 of the leg 11 by setting a flexion selector 9 to the desired angle of flexion along the second setting area 2. This prior art system, however, is potentially confusing to the patient when setting the desired range of motion. Such a hinge brace does not provide an intuitive interface for the patient to set a range of motion of the assembled brace.

Furthermore, the setting of the range of motion in prior art knee braces can require complex movement of the setting mechanism and, at the very least, is cumbersome. Adjusting prior knee braces requires manipulating a setting selector using both hands. Prior braces require the use of two fingers to adjust the setting, one at the top and one at the bottom, which makes it more difficult to adjust the angle while such a brace is on. This makes it difficult for a patient to adjust the knee brace while wearing it. This also prevents quick and easy adjustment or readjustment of the knee brace hinge.

Additionally, post operative knee braces should fit on patients of varied sizes and be customizable in this way. It is desirable to make a post operative knee brace which can accommodate all types of patients. This can be accomplished by telescopic expansion of the knee brace, which allows the brace to be fitted to a variety of body sizes. However, prior art methods of telescopic expansion in knee braces require complex spring loaded locking and multiple separate components, complicating and increasing the costs of production.

DETAILED DESCRIPTION OF THE PREFERRED EMBODIMENT

Figure 1:
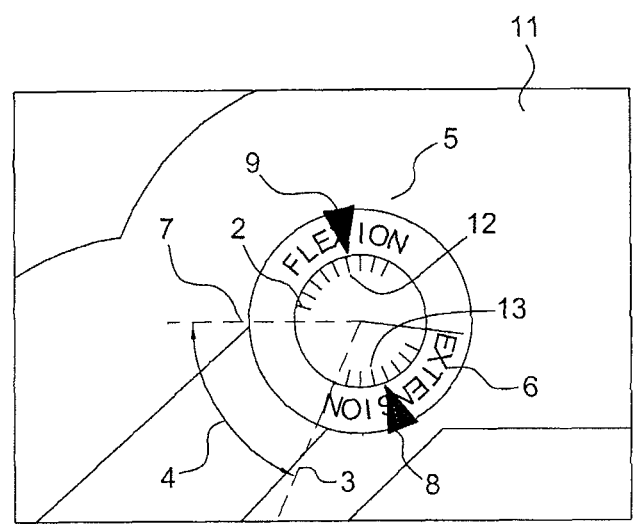
FIG. 1 is a prior art post operative knee brace.
Figure 2A:
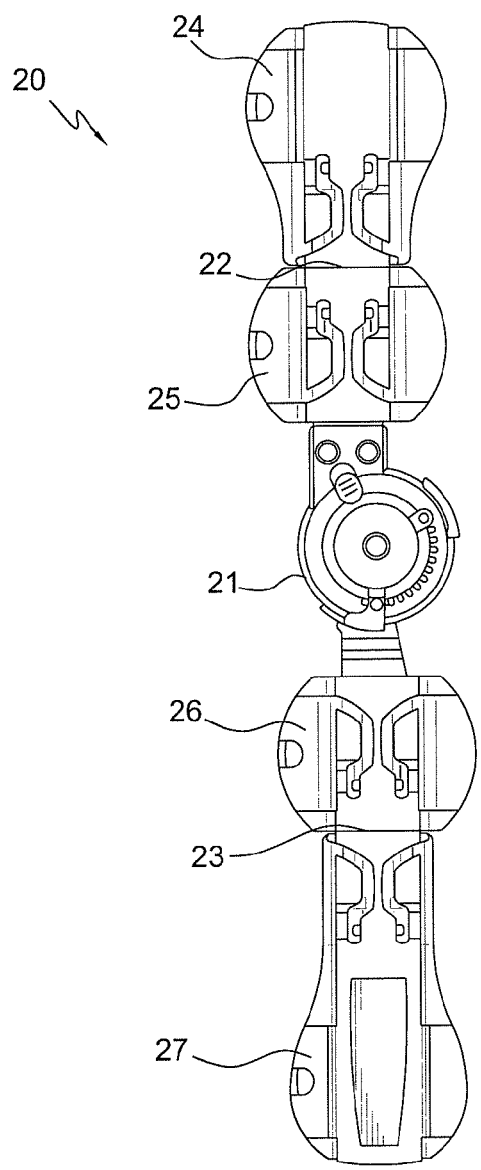
FIG. 2a is a front view of an embodiment of the hinge brace.
Figure 2B:
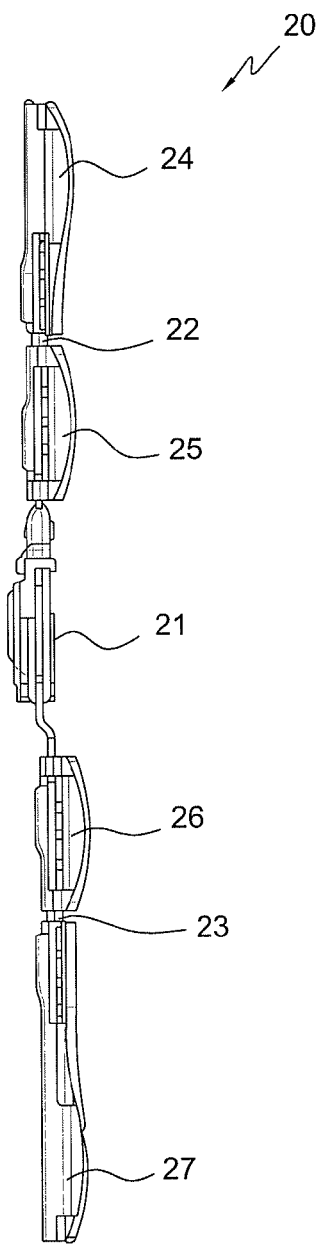
FIG. 2b is a side view of the embodiment shown in FIG. 2a, rotated 90°.

The invention relates to a brace and methods of using such a device. Such a system provides a user an intuitive interface for setting and controlling the range of motion of a joint the brace supports. The hinge brace provides for one handed or even single fingered adjustment of the brace in this way. Furthermore, the brace system provides telescopic expansion of the hinge brace without the need for complicated components. An embodiment of the hinge/hinge brace system is a post-operative hinge brace used to support a knee joint is shown in FIGS. 2a and 2b. Other embodiments of the brace can be used with other joints, such as the hip and elbow.

The post-operative hinge brace 20 embodiment, shown in FIGS. 2a and 2b, has a hinge 21, which allows for easy and intuitive control of brace support settings, one handed or single fingered adjustment of the hinge brace 20, and a telescopic expansion system which makes the hinge brace 20 wearable by users of varied physical dimensions.

As shown in FIGS. 2a and 2b, the hinge brace 20 includes a hinge 21, an upper leg bar 22, a lower leg bar 23, and sliding members 24, 25, 26, and 27. As depicted in FIGS. 2a and 2b, sliding members 24 and 25 slide over the upper leg bar 22 and sliding members 26 and 27 slide over the lower leg bar 23. Sliding members 24, 25, 26, and 27 can be positioned along the upper or lower leg bars 22 and 23 to fit the dimensions of a particular patient.

Figure 3:
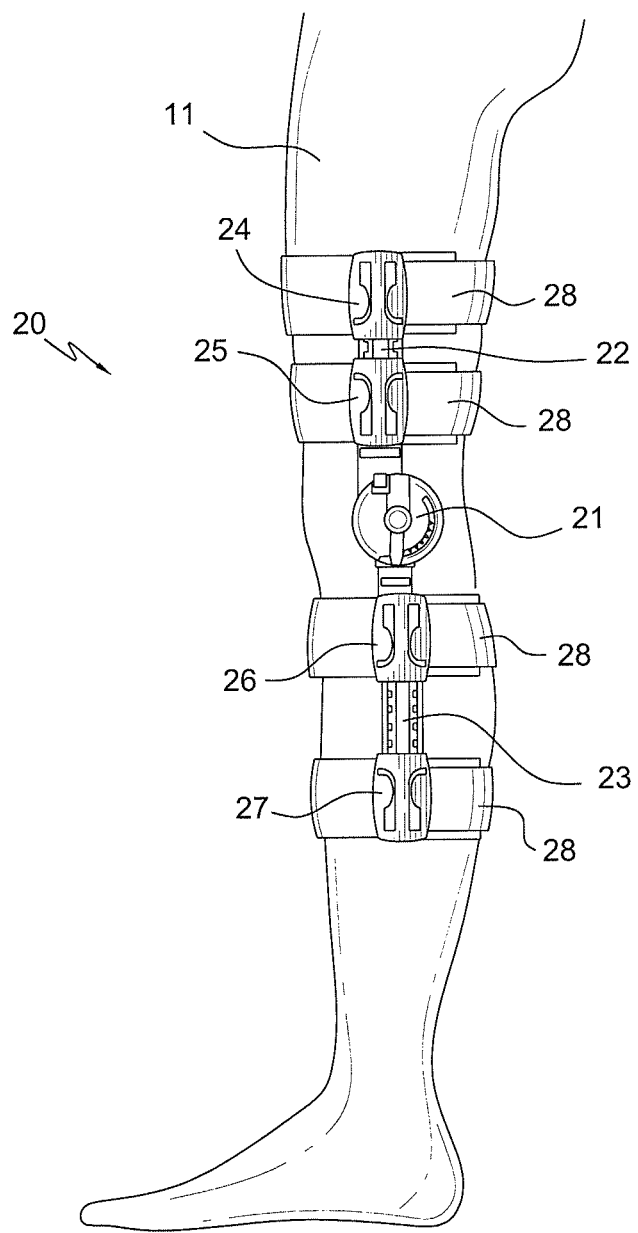
FIG. 3 provides a view of an embodiment of the hinge brace as worn by a patient.

FIG. 3 depicts a hinge brace 20 as worn on the left leg 11 of a patient. The hinge brace 20 can include a plurality of straps 28 for attaching the brace 20 to the patient's leg 11. These straps 28 can be attached to the hinge brace 20 by sliding members 24, 25, 26, and 27. Sliding members 24 and 25 can be attached to the upper leg bar 22 above the hinge 21 for use on the upper potion (thigh) of the leg 11. Sliding members 26 and 27 can be attached to the lower leg bar 23 below the hinge 21 for use on the lower portion (calf) of the leg 11. The straps 28 can attach to themselves via hook and loop fasteners or other suitable fasteners so that they are adjustable for varied user physical dimensions.

Figure 4:
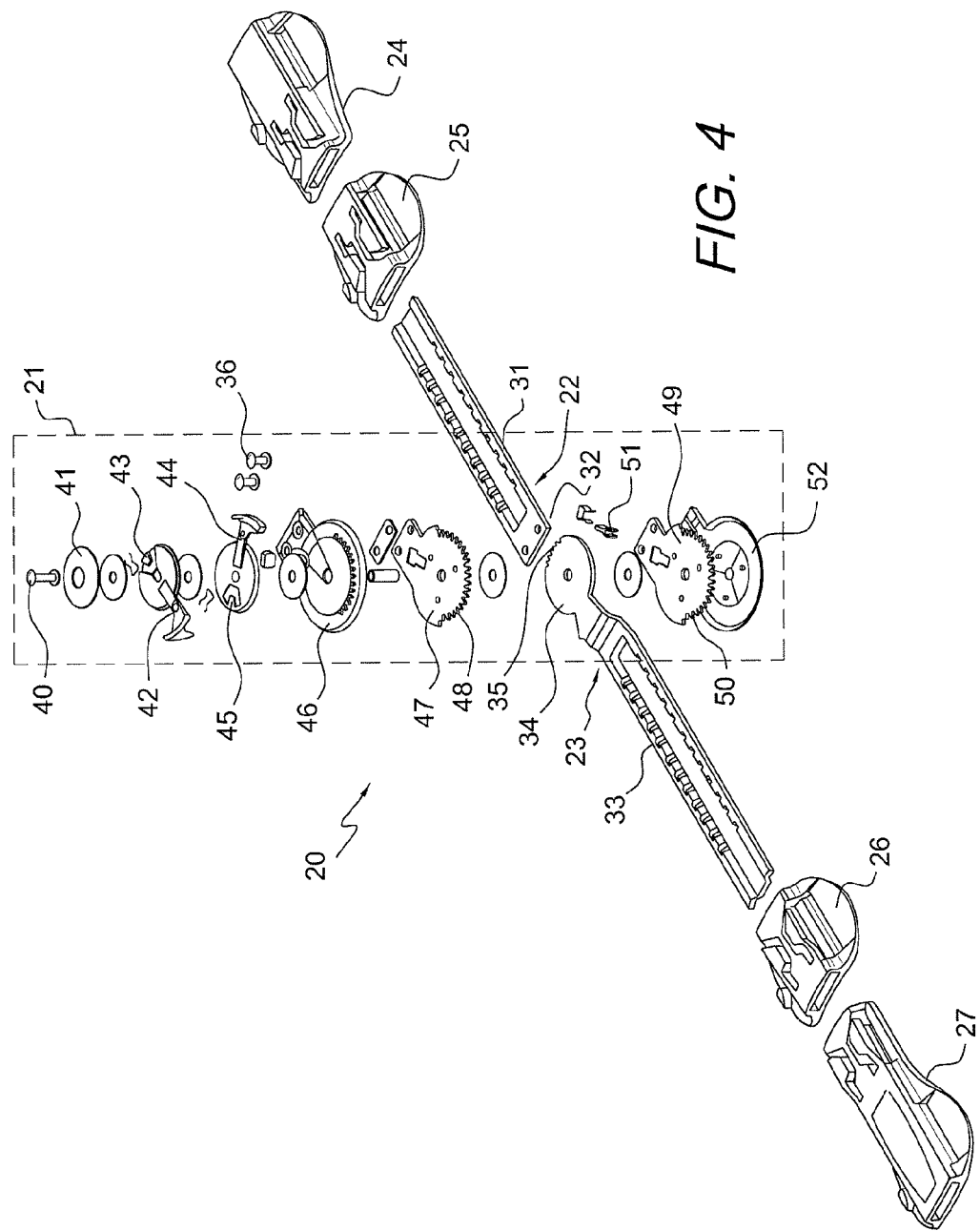
FIG. 4 provides an exploded view of a hinge brace and its components.

FIG. 4 provides an exploded view of the hinge brace 20. The hinge brace 20 includes the upper leg bar 22 and the lower leg bar 23. As discussed above in relation to FIG. 3, sliding members 24 and 25 slide over and lock to upper leg bar 22, while sliding members 26 and 27 slide over and lock to lower leg bar 23. The upper leg bar 22 has a bar potion 31 and can be permanently or removably attached to the hinge 21 at points 32, e.g., with rivets 36. The lower leg bar 23 has a bar portion 33 and lower bar hinge portion 34. Lower bar hinge portion 34 also comprises teeth 35, and can be integrally formed with to the hinge 21 at a central hub 40 such that lower hinge bar 23 may rotate about the hinge 21. Leg bars 22 and 23 can be flat aluminum or can be formed in an I-beam type of construction for added strength. When formed in an I-beam type of construction, leg bars 22 and 23 are concave, in the sense that they bend away from the leg 11 of the patient and the indentation is toward the patient.

The hinge 21, outlined by a dashed box in FIG. 4, includes a central hub 40. A top cap 41, a first setting arm 42 with spring 43, a second setting arm 44 with spring 45, a front plate 46, a first hinge plate 47 with teeth 48, a second hinge plate 49 with teeth 50, and a bottom plate 52 are attached to the central hub in that order. A toothed slider 51 is included as a locking mechanism. Other embodiments can be similarly arranged.

Figure 5A:
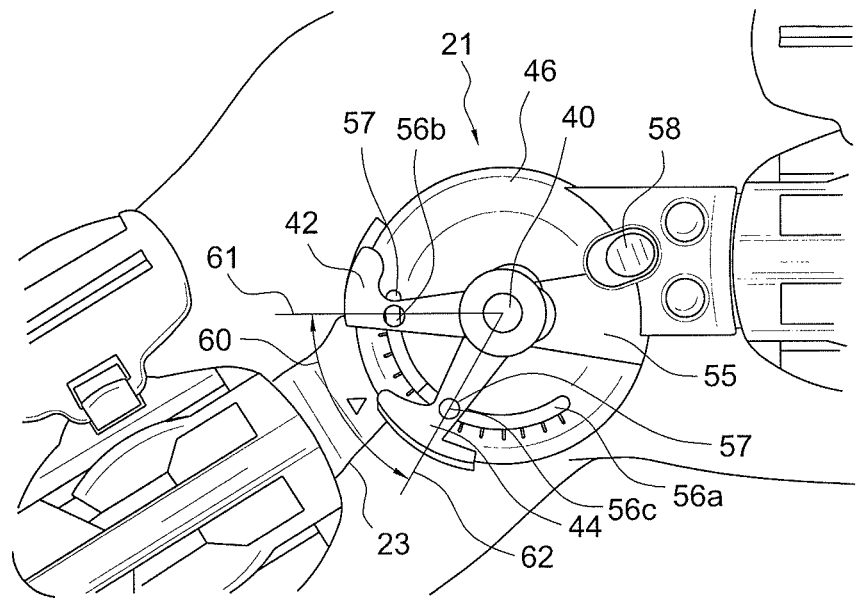
FIG. 5a depicts an embodiment of the hinge of a hinge brace.
Figure 5B:
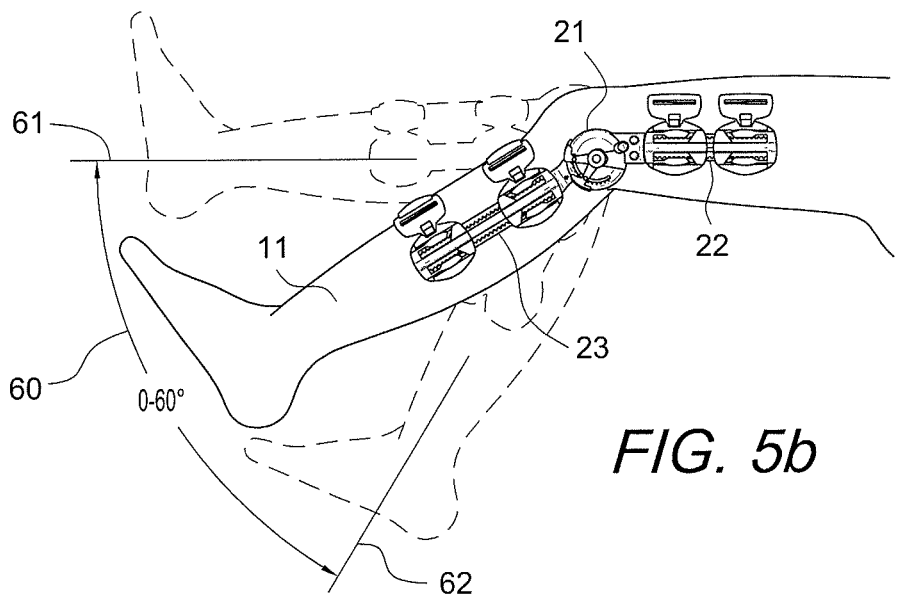
FIG. 5b depicts the functionality of an embodiment of the hinge of a hinge brace.

FIGS. 5a and 5b show the general operation and features of a hinge 21, where FIG. 5a shows a close-up view of the hinge 21 and FIG. 5b provides a perspective of the hinge 21 as being used on a patient's leg 11. In the following examples, the hinge brace 20 is adjusted and set to provide a maximum leg extension angle of 0° (which would allow full extension) and a maximum leg flexion angle of 60° (which would limit the leg flexion to flex approximately 60° from totally extended), although it should be understood that the maximum angles of extension and flexion can be set to any angle (e.g., between full extension and full flexion of the joint).

As shown in FIG. 5a, the hinge 21 comprises a first setting arm 42 and a second setting arm 44. In this embodiment, the setting arms 42 and 44 are designed to visually represent the lower portion of the patient's leg 11 and an upper leg visual cue 55 is likewise provided on the hinge 21 to represent the upper portion of a patient's leg 11. By depicting the effect of actual leg position (or other body parts for other joint embodiments) on the top plate 46 of the hinge 21, it becomes very easy for the user to relate the range of motion set and the actual movement of the leg 11. This arrangement helps in visually communicating the permissible angle of the leg 11, unlike prior art braces.

The hinge 21 controls the maximum extension 61 and maximum flexion 62, corresponding to a range of movement 60 for the leg 11. The maximum extension 61 and maximum flexion 62 can be adjusted using a first setting arm 42 and a second setting arm 44. To facilitate proper angle settings, angle markings 56a are provided on the hinge 21. First setting arm 42 and second setting arm 44 can have transparent portions, which may be cutouts, 57 so that angle markings 56b and 56c can be viewed through the setting arms 42 and 44, respectively. The two setting arms 42 and 44 slide outside of the top plate 46 of the hinge 21, and rotate around the central hub 40 of the hinge 21. The first setting arm 42 and second setting arm 44 share and rotate about the same central hub 40. In this example, first setting arm 42 controls the maximum extension of the leg 11, represented by line 61. Second setting arm 44 controls the maximum flexion of the leg 11, represented by line 62. As shown in FIG. 5a, the first setting arm 42 is positioned at the 0° angle marking 56b and second setting arm 44 is position at the 60° angle marking 56c, creating a range of motion 60 for the leg 11 of about 60°. Operation of the setting arms 42, 44 is explained in greater detail below in reference to FIG. 6.

The hinge 21 can also have a push button 58 for rapidly locking and immobilizing the hinge 21. Referring to FIGS. 4 and 5a, the push button 58 can be slid towards the center hub 40, causing toothed slider 51 to engage the teeth 35 of the lower leg bar hinge 34. The lower leg bar 23, which rotates around central hub 40 via lower leg bar hinge 34, has teeth 35 facing toothed slider 51. Toothed slider 51 prevents the hinged portion 34 of lower leg bar 23 from rotation by engaging and locking the teeth 35 of the lower bar hinge 23, thus immobilizing hinge brace 20.

As shown in FIG. 5b, setting the first and second setting arms 42, 44 prevent the patient's leg 11 from extending and flexing beyond a maximum extension 61 and maximum flexion 62, creating a range of motion represented by an angle 60. In the described embodiment, lower hinge bar 23 rotates within the hinge 21 between the maximum extension 61 and maximum flexion 62, forming range of motion 60, while upper hinge bar 22 does not rotate and is fixed to the hinge. As described, the hinge 21 visually communicates the two extreme permissible leg positions, i.e., the extension and flexion.

This hinge 21 makes the product very interactive, more user-friendly and self-explanatory for a user, both advantages for a device that is to be both used and operated by patient-users, typically not having any specialized training.

Figure 6:
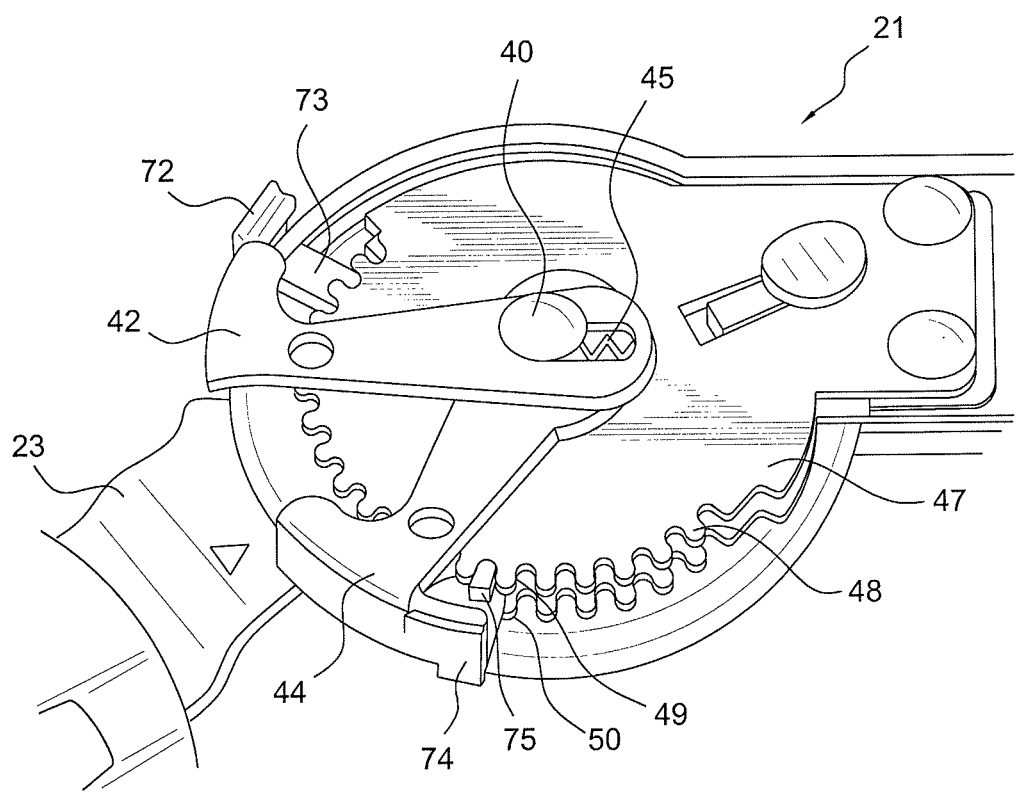
FIG. 6 depicts internal components of an embodiment of the hinge.

Setting the maximum extension and maximum flexion is shown in FIG. 6, which shows components of a hinge 21. Both setting arms 42, 44 are rotatably connected at the center hub 40 of the hinge 21. The first setting arm 42 has a first extended portion 72 with first extended portion teeth 73. The second setting arm 44 has a second extended portion 74 with second extended portion teeth 75. The first extended portion 72 and second extended portion 73 can be approximately the same thickness as the hinge 21, spanning approximately the distance between top plate 46 and bottom plate 52 along the edge of the hinge 21. As shown in FIG. 6, first extended portion teeth 73 engage the teeth 48 of first hinge plate 47, locking first extended portion 72 and first setting arm 42 to that position. Second extended portion teeth 75 engage the teeth 50 of second hinge plate 49, locking second extended portion 74 and second setting arm 44 to that position.

Locking of the setting arms 42, 44 prevents the lower leg bar 23 from being rotated past a specific range of motion. The extended portions 72 and 74 of the arms 42, 44 provide the stopping mechanism for limiting rotation of lower leg bar 23. Briefly returning to FIG. 4, lower leg bar 23 has lower leg bar hinge 34, which rotates about the central hub 40 of the hinge 21. Lower leg bar hinge 34 is sandwiched between first hinge plate 47 and second hinge plate 49, and is an internal component of hinge 21. Thus, lower leg bar 23 rotates about the central hub 40, within the hinge 21. Returning to FIG. 6, the extended portions 72 and 74 provide physical barriers which prevent lower leg bar 23 from rotating past the set maximum extension angle 61, and maximum flexion angle 62.

The settings arms 42, 44 are flexible and downwardly biased towards the plates to engage and lock the hinge 21. The setting arms 42, 44 can be disengaged with single finger pressure upwards to adjust the hinge 21. The setting arms 42 and 44 are biased, by spring or otherwise, to maintain engagement of first extended portion 72 to first hinge plate 47, second extended portion 74 to second hinge plate 49. A first spring 45 for the first setting arm 42 can pull the first setting arm 42 towards the center hub 40, maintaining the position of first setting arm 42 and first extended portion 74 through the engagement of first extended portion teeth 73 with first hinge teeth 48. A second spring (not shown and covered by first setting arm 42) for the second setting arm 44 can pull the second setting arm 44 towards the center hub 40, maintaining the position of second setting arm 44 and second extended portion 74 though the engagement of second extended portion teeth 75 with second hinge teeth 50. Other embodiments for other body joints can be similarly arranged.

Figure 7A:
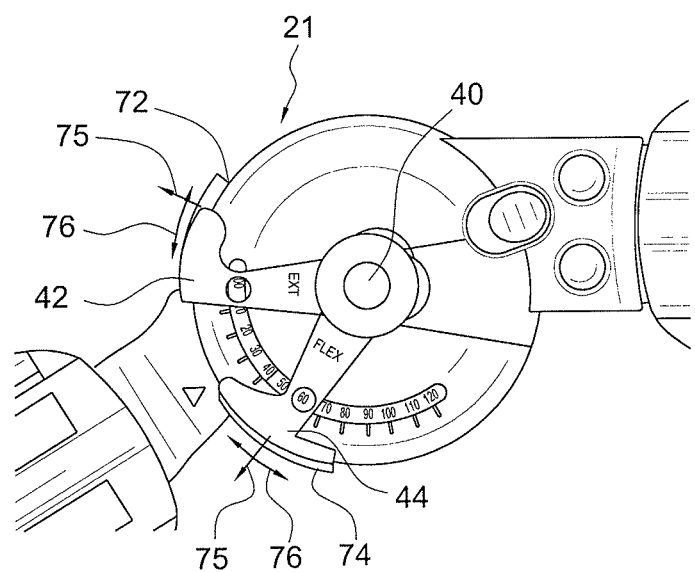
FIGS. 7a and 7b show setting features of an embodiment of the hinge of a hinge brace.

Setting the range of motion for the patient's leg 11 is explained with reference to FIGS. 7a and 7b. Setting the range of motion can be accomplished by unlocking and repositioning the setting arms 42 and 44 and shown in FIG. 7a. The setting arms 42 and 44 are unlocked from their position by pulling the arm 42, 44 in a direction 75 opposing its normal bias towards the hinge teeth 48, 50 by applying pressure, e.g., by finger, on the extended portions 72 and 74. Once the setting arms 42 and 44 are pulled outward, they can then be slid and rotated in radial direction 76 around hinge 21 from their pivot point at the hub 40. Because adjustment is accomplished by pulling 75 and sliding 76 extended portions 72 and 74, inadvertent readjustment is prevented. When the extended portions 72 and 74 are released the setting arms 42 and 44 are locked by biased-action.

Figure 7B:
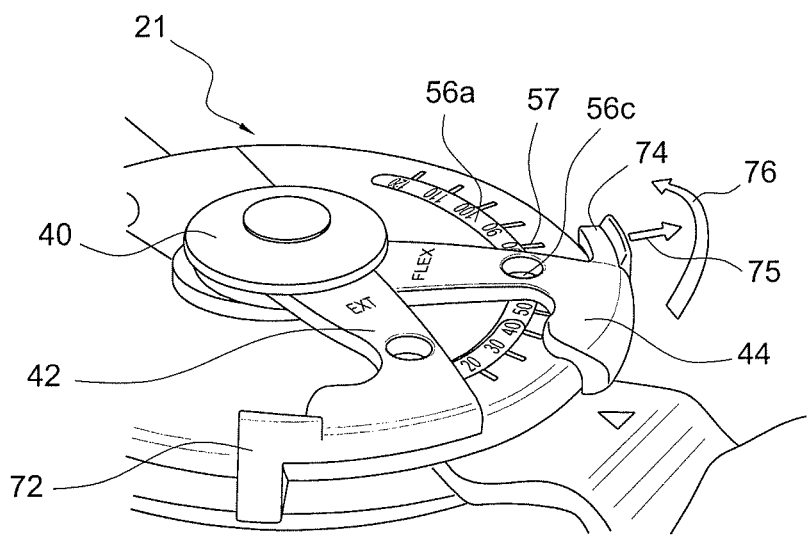

FIG. 7b illustrates setting the hinge 21 to a maximum degree of flexion by setting the setting arm 44. To reposition second setting arm 44, the extended portion 74 is pulled in direction 75 opposing its bias and then slid in direction 76 along the outer edge of the hinge 21 to the desired angle setting along angle markings 56a. The transparent portion 57 of second setting arm 44 allows the patient-user to see the maximum degree of flexion 56c through the second setting arm 44. As the second setting arm 44 is biased, e.g., by spring, it locks the second extended portion 74 at that desired angle setting 56c when it is released, preventing any accidental change in the angle settings. The first setting arm 42 can be repositioned in a similar manner.

Because of the simple pull and slide adjustment mechanism, the angle of rotation can be set using a single finger. This allows adjustment of the hinge 21 even while the hinge brace 20 is on the leg 11. This is a significant advantage of the invention.

Figure 8:
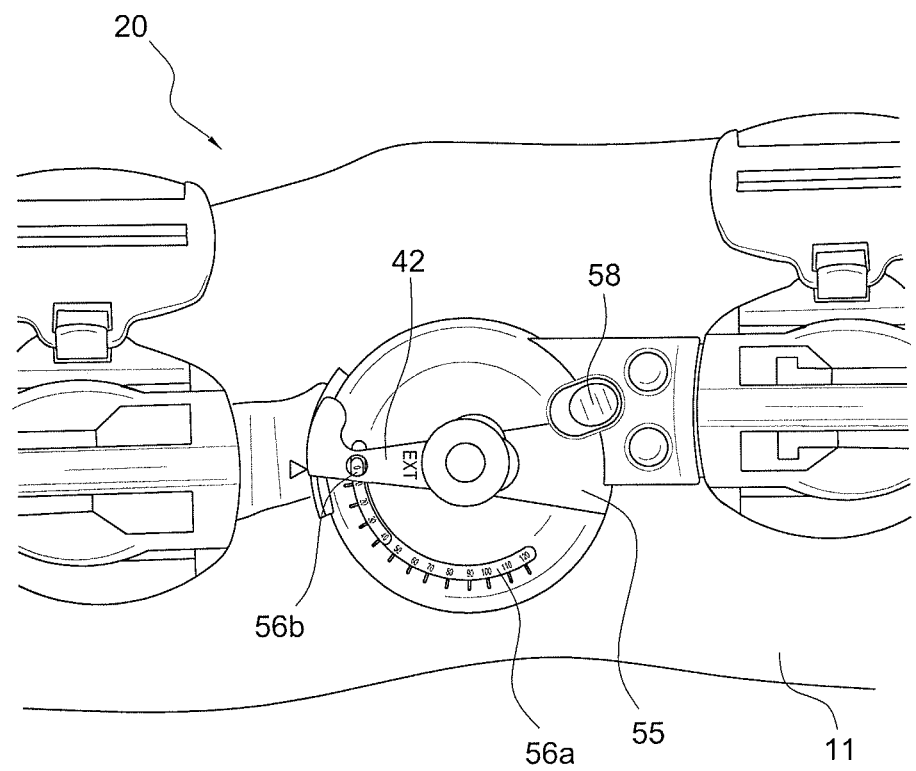
FIG. 8 depicts an embodiment of the hinge brace set to immobilize a patient's leg.

Furthermore, the joint can be locked at a single particular angle by setting the first and second setting arms 42 and 44 to overlap at the same setting, as shown in FIG. 8. In this example, the first setting arm 42 is positioned at a maximum angle of extension 56b of 0°, and the second setting arm 44 (not shown, and covered by first setting arm 42) is positioned at a maximum angle of flexion 56b of 0°. Therefore, the hinge brace 20 does not allow for any range of motion, and locks the leg 11 at a fixed position. Unlike prior knee braces, such a configuration visually and numerically indicates that the joint is locked at one position and there is no permissible movement. The locked position need not be at 0°, as shown in FIG. 8, but can be at any angle 56a on the hinge 21.

Another feature of the hinge brace 20 is telescopic expansion, which provides additional advantages over the prior art. The telescopic expansion of the hinge brace 20 allows for customization of the hinge brace 20 for patients of various physical dimensions. Returning to FIG. 4, the telescopic expansion of the hinge brace 20 is provided by sliding members 24 and 25, which are can be over upper leg bar 22, and sliding members 26 and 27, which can be slid over lower leg bar 23. Sliding members 24, 25, 26, and 27 can be secured at various positions along upper and lower leg bars 22 and 23, providing telescopic expansion.

Figure 9:
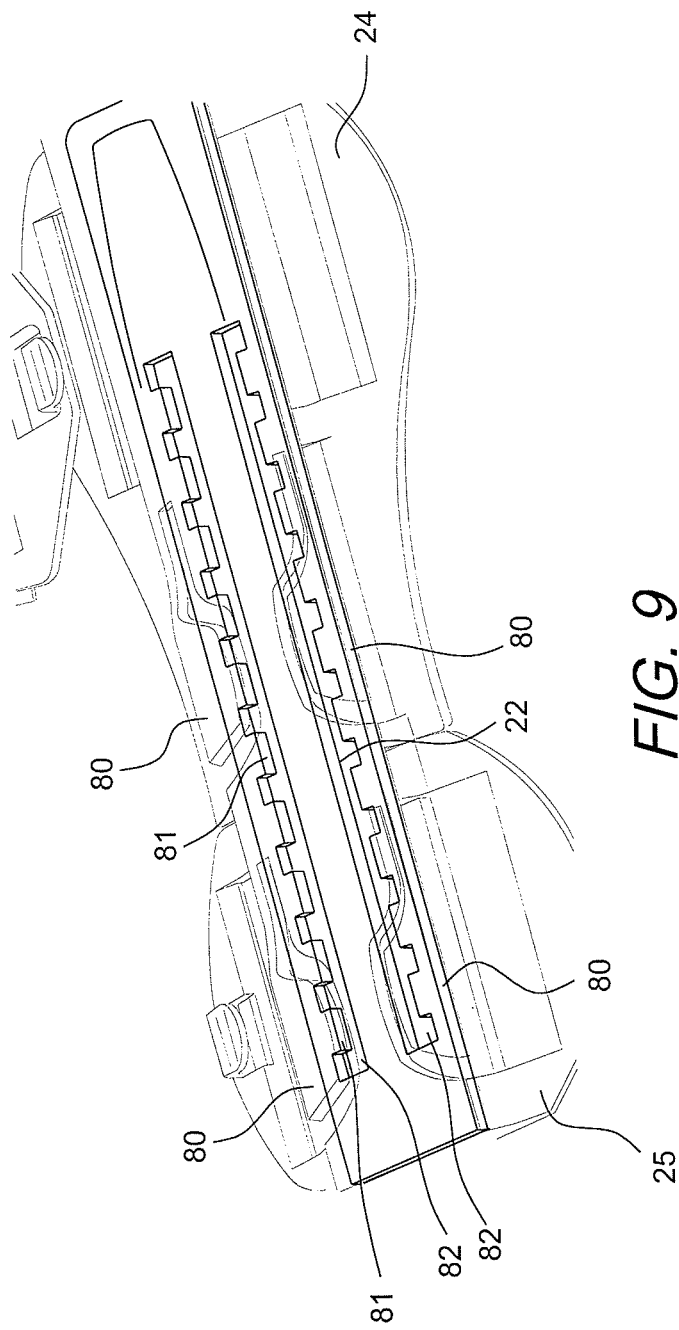
FIG. 9 provides a view of components an embodiment of a hinge brace providing telescopic adjustment of a hinge brace.
Figure 10:
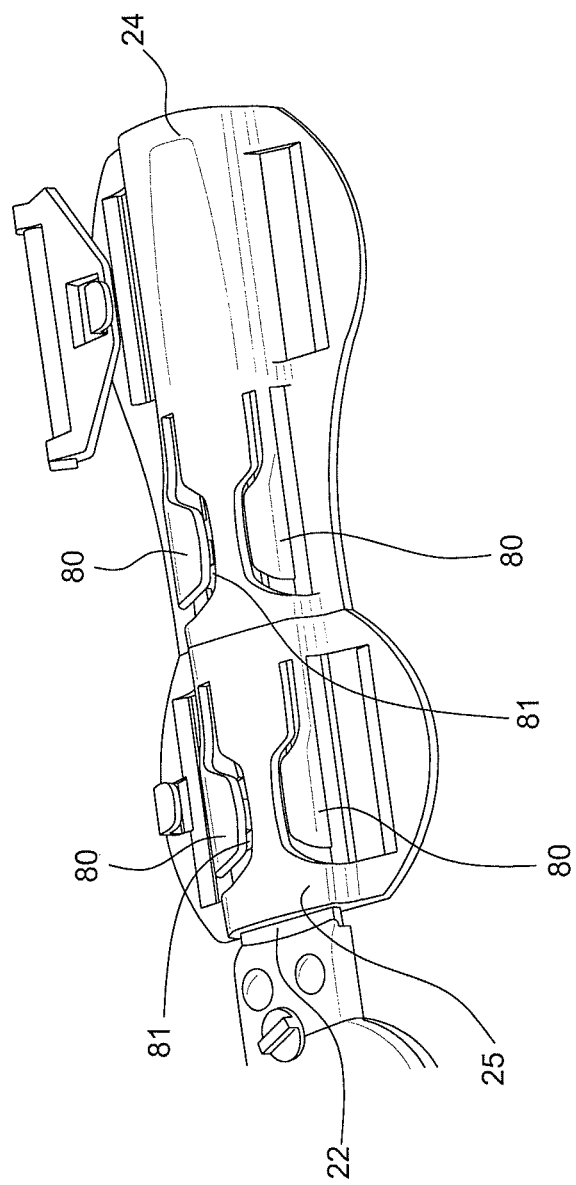
FIG. 10 provides a view of components of an embodiment of a hinge brace providing telescopic adjustment.

FIGS. 9 and 10 depict the sliding members 24, 25 and that engagement with the upper leg bar 22. In FIG. 9 sliding members 24 and 25 are shown as transparent to better show the connection between sliding members 24 and 25 and upper leg bar 22. Sliding members 24, 25 can be single piece components positioned over upper leg bar 22 and can have a locking system that allows them to be adjustably locked at any position along the upper leg bar 22. Unlike prior braces, the present hinge brace 20 does not require spring biased locking and separate components for the telescopic expansion setting. As shown in FIG. 10, sliding members 24 and 25 have flexible areas 80. The flexible areas 80 work as a snap because they are biased to engage parts of the bar 22. The flexible areas 80 of sliding members 24 and 25 have projecting parts at the bottom 81. As shown in FIG. 9, the upper leg bar 22 has teeth 82 that receive and engage the projecting parts 81 of the sliding members. Applying force on flexible areas 80 causes the projecting parts 81 to unlock from hinge bar teeth 82 for adjustment. This locks the sliding members into position. This configuration allows the sliding members to be locked at any position along the bars, without the need for springs. A similar telescopic extension mechanism can be used for the lower leg bar 23 and sliding members 26 and 28. As shown in FIG. 10, the sliding members 24 and 25 can be made of a single piece of material, e.g., plastic or metal. This makes the sliding members simple to manufacture and durable.

Alternatively, the locked-in sliding members can be unlocked from the leg bar by using a dual push button system. The leg bars may comprise a system that requires the flexible areas 80 and projecting parts 81 to be actively engaged with the bar teeth 82 by the user, such that when the dual push buttons are engaged, it releases the projecting parts of the sliding members from the leg bar's teeth/slots for adjustment.

The above description and drawings are only illustrative of certain preferred embodiments which achieve the objects, features and advantages of the present invention. The disclosed preferred embodiments most specifically illustrate the configuration relating to a hinge brace for the knee; however, the features shown can be adapted for other embodiments as well, such as an elbow brace and a hip brace. It is not intended that the present invention be limited to these versions but only by the claims.

What is claimed is:

1. A hinge brace comprising:
   a central hub of a hinge;
   a range of motion indicator;
   a first toothed hinge plate;
   a second toothed hinge plate;
   a first setting arm; and
   a second setting arm, wherein the first setting arm and second setting arm are attached to the central hub such that the first setting arm and second setting arm can rotate about the central hub and along the range of motion indicator for controlling extension and flexion of a joint,
   the first setting arm is biased in a first direction towards the central hub of the hinge to engage the first toothed hinge plate, the second setting arm is biased in a second direction towards the central hub of the hinge to engage the second toothed hinge plate,
   the first setting arm can be disengaged from the first toothed hinge plate when said first setting arm is pulled in a third direction radially outward from the central hub of the hinge, and
   the second setting arm can be disengaged from the second toothed hinge plate when said second setting arm is pulled in a fourth direction radially outward from the central hub of the hinge;
   the hinge brace further comprising:
   a first bar with a first set of receiving teeth; and
   a first sliding member with a first flexible area and a first projecting part on the first flexible area, wherein the first sliding member is a single piece of material and configured to slide over the first bar,
   the first projecting part is configured to engage the first set of receiving teeth in a first lateral direction away from a centerline of a longitudinal length of the first bar, and is biased in said first lateral direction to the first set of receiving teeth,
   and the first projecting part is movable in a direction opposed to the first lateral direction toward the centerline of the longitudinal length of the first bar in order to disengage the first projecting part from the first set of receiving teeth.

2. The hinge brace of claim 1, wherein the first setting arm and second setting arm are movable in an outward radial direction.

3. The hinge brace of claim 2, wherein the first setting arm and the second setting arm can be disengaged from the first toothed hinge plate and the second toothed hinge plate with one finger.

4. The hinge brace of claim 1, wherein the first setting arm controls a maximum extension of the hinge brace.

5. The hinge brace of claim 1, wherein the second setting arm controls a maximum flexion of the hinge brace.

6. The hinge brace of claim 1, wherein the first toothed hinge plate and the second toothed hinge plate substantially overlap.

7. The hinge brace of claim 6, wherein the toothed portion of the first toothed hinge plate and the toothed portion of the second hinge plate are substantially along a same arc with respect to the central hub.

8. The hinge brace of claim 1, wherein the hinge further comprises a push button locking mechanism that immobilizes the flexion and extension of the hinge brace.

9. The hinge brace of claim 1, wherein the hinge brace further comprises a visual depiction of an upper leg, the first setting arm provides a first visual depiction of a lower leg, and the second setting arm provides a second visual depiction of a lower leg.

10. The hinge brace of claim 1, wherein the hinge brace further comprises:
a second bar with a second set of receiving teeth; and
a second sliding member with a second flexible area and a second projecting part on the second flexible area, wherein the second sliding member is a single piece of material configured to slide over the second bar,
the second projecting part is configured to engage the second set of receiving teeth in a second lateral direction away from a centerline of a longitudinal length of the second bar, and is biased in said second lateral direction to the second set of receiving teeth,
and the second projecting part is movable in a direction opposed to the second lateral direction toward the centerline of the longitudinal length of the second bar in order to disengage the second projecting part from the second set of receiving teeth.

11. The hinge brace of claim 10, wherein the first bar and second bar are each I-beams, concave relative to the leg.

12. The hinge brace of claim 10, wherein the first bar is statically affixed to the hinge and the second bar is attached to the central hub such that it can rotate about the hub.

13. The hinge brace of claim 1, wherein the hinge brace further comprises:
a third sliding member with a third flexible area and a third projecting part on the third flexible area, wherein the third sliding member is a single piece of material configured to slide over the first bar,
the third projecting part is configured to engage the first set of receiving teeth in the first lateral direction away from a centerline of a longitudinal length of the first bar, and is biased in said first lateral direction to the first set of receiving teeth,
and the third projecting part is movable in the a direction opposed to the first lateral direction toward the centerline of the longitudinal length of the first bar in order to disengage the third projecting part from the first set of receiving teeth.

14. The hinge brace of claim 13, wherein the hinge brace further comprises:
a second bar with a second set of receiving teeth;
a second sliding member with a second flexible area and a second projecting part on the second flexible area; and
a fourth sliding member with a fourth flexible area and a fourth projecting part on the fourth flexible area, wherein the second sliding member and fourth sliding member are a single piece of material and are configured to slide over the second bar,
the second and fourth projecting parts are configured to engage the second set of receiving teeth in the second lateral direction away from a second centerline of a longitudinal length of the second bar, and is biased in said second lateral direction to the second set of receiving teeth,
and the second and fourth projecting parts are movable in a direction opposed to the second lateral direction toward the second centerline in order to disengage the second and fourth projecting parts from the second set of receiving teeth.

15. The hinge brace of claim 1, wherein the first bar is an I-beam, concave relative to the leg.

16. The hinge brace of claim 1, wherein the first sliding member is a plastic material.

17. The hinge brace of claim 1, wherein the first sliding member is a metal material.

18. The hinge brace of claim 1, wherein the first sliding member further comprises a strap for affixing the hinge brace to a patient.

19. A method of operating a hinge brace comprising:
rotating a first setting arm around a central hub;
rotating a second setting arm around the central hub;
biasing the first setting arm in a first direction towards the central hub to engage the first toothed hinge plate;
biasing the second setting arm in a second direction towards the central hub to engage the second toothed hinge plate;
controlling the extension of a joint by setting the first setting arm along a range of motion indicator;
controlling the flexion of a joint by the setting second setting arm along the range of motion indicator;
disengaging the first setting arm and second setting arm from the first toothed hinge plate and the second toothed hinge plate for adjustments by pulling the first and second setting arms in a direction away from the central hub;
sliding a first sliding member over a first bar, wherein the first bar comprises a first set of receiving teeth, and wherein the first sliding member is a single piece of material comprising a first flexible area and a first projecting part on the first flexible area;
biasing the first projecting part in a first lateral direction away from a centerline of a longitudinal length of the first bar to engage the first set of receiving teeth; and
disengaging the first projecting part from the first set of receiving teeth by moving the first projecting part in a direction opposed to the first lateral direction toward the centerline of the longitudinal length of the first part.

20. The method of claim 19, further comprising disengaging the first setting arm from the first toothed hinge plate with at least one finger.

21. The method of claim 19, further comprising immobilizing flexion and extension of the hinge brace by using a push button locking mechanism.

22. The method of claim 19, further comprising immobilizing the flexion and extension of the hinge brace by setting the first setting arm and the second setting arm at substantially the same setting along the range of motion indicator.

\* \* \* \* \*